(12) United States Patent
Bartschi

(10) Patent No.: US 6,254,824 B1
(45) Date of Patent: Jul. 3, 2001

(54) **METHOD FOR CONTROLLING *MYXOBOLUS CEREBRALIS***

(75) Inventor: James A. Bartschi, Telluride, CO (US)

(73) Assignee: Scott Fly Rod Company, Telluride, CO (US)

( * ) Notice: Subject to any disclaimer, the term of this patent is extended or adjusted under 35 U.S.C. 154(b) by 0 days.

(21) Appl. No.: 09/140,906

(22) Filed: Aug. 27, 1998

(51) Int. Cl.[7] .................................................. A61L 2/00
(52) U.S. Cl. .................................. 422/28; 422/6; 422/37
(58) Field of Search ................................ 422/6, 28, 37, 422/40, 292

(56) References Cited

U.S. PATENT DOCUMENTS

| | | | |
|---|---|---|---|
| 4,933,341 | * | 6/1990 | Lindner et al. ....................... 514/241 |
| 5,320,805 | * | 6/1994 | Kramer et al. .......................... 422/28 |
| 5,424,323 | * | 6/1995 | Wachman et al. .................... 514/358 |

* cited by examiner

*Primary Examiner*—Krisanne Thornton
(74) *Attorney, Agent, or Firm*—Marshall & Melhorn, LLC

(57) ABSTRACT

A method for controlling the spread of the parasitic microorganism, *Myxobolus cerebralis*. The method involves the application of a solution containing a quaternary ammonium compound onto articles carrying *Myxobolus cerebralis* in order to the destroy the microorganism.

20 Claims, 1 Drawing Sheet

METHOD FOR CONTROLLING *MYXOBOLUS CEREBRALIS*

BACKGROUND OF THE INVENTION

1. Field of the Invention

This invention relates to a method for controlling *Myxobolus cerebralis*, more particularly the invention relates to the application of a solution onto articles carrying *Myxobolus cerebralis* in order to neutralize the *Myxobolus cerebralis* carried thereon. Even more particularly, this invention is directed toward the application of a solution containing a quaternary ammonium compound on articles, such as fishing equipment and accessories, to prevent the spread of *Myxobolus cerebralis* in cold water fisheries.

2. Summary of Related Art

*Myxobolus cerebralis* is known to cause whirling disease in salmonids in North American waterways as well as in other cold water fisheries around the world. The spread of whirling disease poses a significant threat to the species and to sport fishing in general. In particular, certain salmonids, such as rainbow trout, are especially susceptible to the disease.

Whirling disease is a descriptive term which indicates the effect of a parasitic microorganism, *Myxobolus cerebralis*, on immature salmonids. *Myxobolus cerebralis* may also be generally referred to as *Myxosoma cerebralis*. For purposes of this invention the terms are intended to mean the same or similar microorganism.

The spores of *Myxobolus cerebralis* infect the salmonids through the skin of the fish. The parasite effects the growth of the fish by attacking their nervous system. The symptoms include the blackening of the tails of the infected fish as well as a whirling behavior or whirling movements. Additionally, the heads and spine of the fish infected with the parasite can develop improperly and result an unnatural curvature in the body of the fish. The salmonid is then unable to swim properly to survive.

*Myxobolus cerebralis* spores can be found on underwater objects and in the mud and silt along waterways. *Myxobolus cerebralis* is known to take on two different forms. One form is found in water systems and is generally eaten by aquatic worms (*Tubifex tubifex*). A second form, is apparently released by the aquatic worms where it infects the salmonids. The second form may also be introduced to the salmonids through ingestion of the worms.

The spores of the *Myxobolus cerebralis* can be carried away from a contaminated waterway on the exposed surface of objects present in the water such as boots, waders, and other fishing equipment. It is possible for the spores to survive on the contaminated equipment for an extended period of time under proper conditions. Some studies have indicated that *Myxobolus cerebralis* remains viable in the dried mud for several years. The continued use of the contaminated equipment could cause the additional spread of *Myxobolus cerebralis* in other uncontaminated waterways. Therefore, it is desirable to clean and disinfect the contaminated equipment in order to prevent the further spread of *Myxobolus cerebralis*.

Disinfectants, antimicrobials, and germicides are generally recognized in the art to clean surfaces in various commercial, residential and institutional applications. However, the development and use of an effective solution to prevent the transportation of spores of *Myxobolus cerebralis* on articles exposed to the microorganism has not been recognized in the art.

Thus, it would be an advantage to provide a method for controlling the spread of *Myxobolus cerebralis* in waterways. The contamination of the waterways can be attributed to the carrying and transportation of the spores of the parasitic microorganism on articles that have been in contact with the spores in contaminated waterways and fisheries.

SUMMARY OF THE INVENTION

In accordance with the present invention, there is provided a method for controlling the spread of *Myxobolus cerebralis* in waterways. The present inventive method utilizes a solution that can be applied onto contaminated articles to neutralize spores of *Myxobolus cerebralis*.

The method of the present invention includes the application of a solution onto articles containing a quaternary ammonium compound as an active ingredient. The quaternary ammonium compound is effective in neutralizing, or killing, the spores of *Myxobolus cerebralis* that are located on the article.

The quaternary ammonium compound is preferably selected from the group consisting of alkyl benzyl dimethyl ammonium chloride and tetradecyl benzyl dimethyl ammonium chloride. The compounds are preferably included in amount greater than 800 ppm.

It is desirable, through the practice of the present inventive method, to control the spread of *Myxobolus cerebralis* by applying a solution containing an active quaternary ammonium compound onto articles carrying *Myxobolus cerebralis* in order to destroy the parasitic microorganism carried thereon.

BRIEF DESCRIPTION OF THE DRAWINGS

The above, as well as other advantages of the present invention, will be become readily apparent to those skilled in the art from the following detailed description when considered in the light of the accompanying drawing in which.

DETAILED DESCRIPTION OF THE PREFERRED EMBODIMENT

Figure 1:
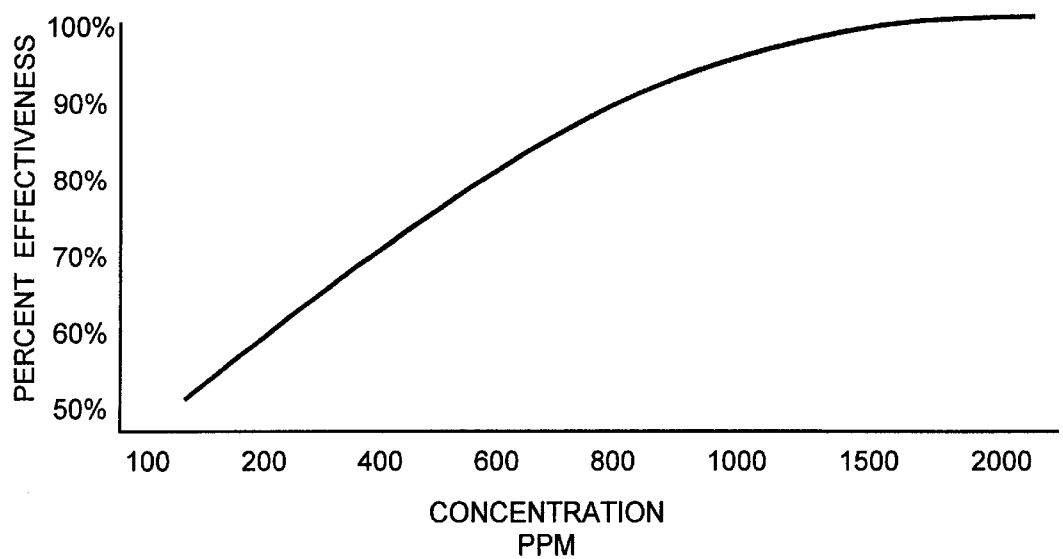
FIG. 1 is a graph indicating the effectiveness of the active ingredient in neutralizing *Myxobolus cerebralis* at various concentrations.

It has been discovered that the application of a solution, containing an active quaternary ammonium compound, onto an article is effective in neutralizing viable spores of *Myxobolus cerebralis* that are contained on the article.

For the purposes of the invention, the term neutralizing indicates the killing or destroying of the parasitic microorganisms that are located on an article. The term *Myxobolus cerebralis* is generally utilized to indicate both the microorganisms and the spores of the microorganism. Additionally, the term is used to indicate the microorganism in general and is not directed to a particular phase or form.

The solution utilized in practicing the present inventive method is generally a water based solution. Water is the preferred carrier for the active ingredient. However, other solvents or solutions may be suitable as well. The relevant feature in selecting the carrier solution is the delivery of the active ingredient onto the article. Additionally, other solvents, such as alcohols or glycols, may be added to the water based solution as diluents or to assist in the evaporation of the carrier solvent upon application of the active ingredient onto the article.

In accordance with the present invention, the active ingredient in the solution is a quaternary ammonium compound. Quaternary ammonium compounds are effective in neutralizing *Myxobolus cerebralis*. The preferred compounds are alkyl benzyl dimethyl ammonium chloride (sold by Spectrum Chemical Company of New Brunswick, N.J., Stepan Company of Northfield, Ill., or by Albemarle Corporation of Baton Rouge, La.) and tetradecyl benzyl dimethyl ammonium chloride (sold as ROCCAL™ by the Hilton-Davis Company of Cincinnati, Ohio). The alkyl groups of the alkyl benzyl dimethyl ammonium chloride compounds can include various carbon chains. For example, the alkyl groups of the alkyl benzyl dimethyl ammonium chloride sold by Spectrum Chemical Company is defined as 40% $C_{12}$, 50% $C_{14}$, and 10% $C_{16}$. Other mixtures and percentages of alkyl compounds having different carbon chain lengths are suitable for use with the present inventive method.

The compounds are preferably added to the solution in an amount greater than about 800 ppm, and most preferably greater than about 1000 ppm. The effectiveness of the active ingredient in killing *Myxobolus cerebralis* at the noted concentration is extremely high. It is even more desirable to maintain the concentration of the active ingredient in the range of about 1200 ppm to about 2500 ppm. The noted concentrations of active ingredient are high enough to neutralize or destroy the microorganism without adversely affecting the article or the environment.

FIG. 1 depicts the efficiency of various concentrations of the preferred compound, alkyl benzyl dimethyl ammonium chloride, in neutralizing *Myxobolus cerebralis*. The graph of FIG. 1 was developed by observing waterborne active spores at room temperature. The spores were subjected to treatment of the active ingredient at various concentrations. Visible distortion of the sporoplasm and polar filaments were interpreted as death or destruction of the spore. As indicated in FIG. 1, concentrations of 800 ppm or greater were more than ninety percent effective in neutralizing the spores.

The solution of the present invention may optionally contain ingredients such as fragrance and dyes for aesthetic reasons. Conventional fragrances and dyes generally recognized in the art may be suitable for use with the invention.

The solution may be applied to various types of articles that are capable of carrying *Myxobolus cerebralis* upon exposure to the microorganism in rivers, lakes and streams. For example, the article could include items such as fishing accessories, boots, shoes, waders, wading shoes, nets, float tubes, and personal watercraft. However, the method of the present invention may be practiced on various other articles that are capable of transporting *Myxobolus cerebralis*.

In practicing the present inventive method, the solution is applied onto the article to neutralize viable *Myxobolus cerebralis* microorganisms carried on the article. The solution may be applied in various fashions. For example, the solution may be sprayed, wiped, brushed or poured onto the article. Alternatively, the article may dipped or immersed in the solution. Conventional equipment generally used for the application of a solution onto an article are suitable for use with the present invention. The important aspect is delivering the active ingredient onto the article in a sufficient amount and manner such that contact is made between the active ingredient and the microorganism. A preferred method of application will often be dependent upon the form of the article.

The following example, which constitute the best mode presently contemplated by the inventors for practicing the present invention, is presented solely for the purpose of further illustrating and disclosing the present invention, and is not to be construed as a limitation on, the invention:

A solution was produced in accordance with the present invention by adding alkyl (40%$C_{12}$, 50%$C_{14}$, 10%$C_{16}$) benzyl dimethyl ammonium chloride to water in an amount sufficient to form a concentration of about 1000 ppm of the active ingredient in the solution. Additionally, citronella extract was added to the solution as a fragrance. The fragrance was present in the solution at about 200 ppm.

The solution was placed into a spray bottle and applied onto various articles that had been in contact with *Myxobolus cerebralis*. The solution was effective in neutralizing *Myxobolus cerebralis*.

In accordance with the provisions of the patent statutes, the present invention has been described in what is considered to represent its preferred embodiment. However, it should be noted that the invention can be practiced otherwise than as specifically illustrated and described without departing from its spirit and scope.

What is claimed is:

1. A method for controlling *Myxobolus cerebralis*, comprising applying a solution containing a quaternary ammonium compound as an active ingredient onto an article in order to neutralize *Myxobolus cerebralis* carried on said article, wherein the quaternary ammonium compound alone is a sporicidal agent.

2. The method as recited in claim 1, wherein said quaternary ammonium compound is selected from the group consisting of alkyl benzyl dimethyl ammonium chloride and tetradecyl benzyl dimethyl ammonium chloride.

3. The method as recited in claim 1, wherein said quaternary ammonium compound is included in said solution in an amount greater than 800 ppm.

4. The method as recited in claim 3, wherein said quaternary ammonium is included in said solution in a range of about 1200 ppm to about 2500 ppm.

5. The method as recited in claim 1, wherein said solution further includes ingredients selected from the group consisting of fragrance and dyes.

6. The method as recited in claim 1, wherein said article includes fishing accessories, boots, shoes, waders, wading shoes, nets, float tubes, and personal watercraft.

7. The method as recited in claim 1, wherein said solution includes an alcohol or glycol.

8. A method for controlling *Myxobolus cerebralis*, comprising applying a solution containing alkyl benzyl dimethyl ammonium chloride as a sole active ingredient, in an amount greater than 800 ppm, onto an article carrying *Myxobolus cerebralis* in order to neutralize said *Myxobolus cerebralis*.

9. The method as recited in claim 8, wherein said alkyl benzyl dimethyl ammonium is included in said solution in a range of about 1200 ppm to about 2500 ppm.

10. The method as recited in claim 8, wherein said solution further includes ingredients selected from the group consisting of fragrance and dyes.

11. The method as recited in claim 8, wherein said article includes fishing accessories, boots, shoes, waders, wading shoes, nets, float tubes, and personal watercraft.

12. The method as recited in claim 8, wherein said solution includes an alcohol or a glycol.

13. The method as recited in claim 8, wherein the solution is applied by spraying, wiping, brushing, or pouring the solution onto the article.

14. The method as recited in claim 8, wherein the solution is applied by immersing or dipping the article in the solution.

15. A method for controlling *Myxobolus cerebralis* in freshwater, comprising applying a solution containing a quaternary ammonium compound as an active ingredient onto an article in order to neutralize *Myxobolus cerebralis* carried on said article.

16. The method as recited in claim 15, wherein said quaternary ammonium compound is selected from the group consisting of alkyl benzyl dimethyl ammonium chloride and tetradecyl benzyl dimethyl ammonium chloride.

17. The method as recited in claim 15, wherein said quaternary ammonium compound is included in said solution in an amount greater than 800 ppm.

18. The method as recited in claim 17, wherein said quaternary ammonium is included in said solution in a range of about 1200 ppm to about 2500 ppm.

19. The method as recited in claim 15, wherein said solution further includes ingredients selected from the group consisting of fragrance and dyes.

20. The method as recited in claim 15, wherein said article includes fishing accessories, boots, shoes, waders, wading shoes, nets, float tubes, and personal watercraft.

* * * * *